United States Patent
Werber et al.

(10) Patent No.: US 10,123,879 B2
(45) Date of Patent: Nov. 13, 2018

(54) SYSTEM AND METHOD FOR NON-BINDING ALLOGRAFT SUBTALAR JOINT IMPLANT

(71) Applicant: WASAS, LLC., Fort Lauderdale, FL (US)

(72) Inventors: Bruce Werber, Fort Lauderdale, FL (US); Terrell Suddarth, New Market, AL (US); Harold Schoenhaus, Delray, FL (US)

(*) Notice: Subject to any disclaimer, the term of this patent is extended or adjusted under 35 U.S.C. 154(b) by 0 days.

(21) Appl. No.: 15/894,102

(22) Filed: Feb. 12, 2018

(65) Prior Publication Data

US 2018/0177601 A1 Jun. 28, 2018

Related U.S. Application Data

(62) Division of application No. 14/985,125, filed on Dec. 30, 2015, now Pat. No. 9,943,414.

(51) Int. Cl.
| | |
|---|---|
| *A61F 2/42* | (2006.01) |
| *A61L 27/36* | (2006.01) |
| *A61F 2/30* | (2006.01) |

(52) U.S. Cl.
CPC .......... *A61F 2/4202* (2013.01); *A61L 27/362* (2013.01); *A61L 27/3683* (2013.01);
(Continued)

(58) Field of Classification Search
CPC ................ A61F 2/42; A61F 2002/4207; A61F 2002/4212; A61F 2002/4215;
(Continued)

(56) References Cited

U.S. PATENT DOCUMENTS

| 4,450,591 A | 5/1984 | Rappaport |
| 4,467,479 A * | 8/1984 | Brody .................. A61B 17/562 |
| | | 128/898 |

(Continued)

OTHER PUBLICATIONS

"Preserving the Posttrapeziectomy Space with a Human Acellular Dermal Matrix Spacer: A Pilot Case Series of Patients with Thumb Carpometacarpal Joint Arthritis", Caroline A. Yao, MC; Chandra V. Ellis, MD; Mayles J. Cohen, MD.; David A. Kulber, MD, FACS; *From the Plastic Surgery Center, Cedars Sinai Medical Center, and Division of Plastic and Reconstructive Surgery, Keck School of Medicine of the university of Southern California, Los Angeles, Calif. Copyright ® 2013 The Authors. Published by Lippincott Williams & Wilkins on behalf of The American Society of Plastic Surgeons.*; DOI: 10.1097/GOX.0b013e3182aa8793; Published online Oct. 29, 2013 www.PRSGO.com.

*Primary Examiner* — Alvin Stewart
(74) *Attorney, Agent, or Firm* — Law Offices of Daniel W. Roberts, LLC

(57) ABSTRACT

Provided is a system and method for providing a non-binding allograft subtalar joint implant for surgical implant into a person's foot proximate to the ankle. This system for repair includes at least one sterile non-binding allograft subtablar joint implant provided as a pre-formed allograft rod plug "ARP" having a diameter about equal to an average width of a canal between a person's talus and calcaneus bones, the ARP being resiliently compressible and flexible. When snuggly disposed between the person's talus and calcaneus bones, the ARP compresses during normal use of the person's foot and maintains the canal in an anatomically correct alignment and reduces a tendency for abnormal motion between the person's talus and calcaneus bones. An associated method of use is also provided.

31 Claims, 8 Drawing Sheets

(52) U.S. Cl.
CPC ........... *A61F 2002/30224* (2013.01); *A61F 2002/30293* (2013.01); *A61F 2002/30971* (2013.01); *A61F 2002/4207* (2013.01); *A61F 2002/4223* (2013.01); *A61F 2310/00365* (2013.01)

(58) Field of Classification Search
CPC ........ A61F 2002/4217; A61F 2002/422; A61F 2002/4223; A61F 2002/30014; A61F 2002/30751; A61F 2/4202; A61L 27/3645; A61L 27/3654; A61B 17/562; A61B 2017/567
See application file for complete search history.

(56) References Cited

U.S. PATENT DOCUMENTS

| | | | |
|---|---|---|---|
| 5,534,028 A * | 7/1996 | Bao | A61F 2/441 606/247 |
| 5,876,452 A * | 3/1999 | Athanasiou | A61F 2/28 424/424 |
| 6,005,161 A * | 12/1999 | Brekke | A61F 2/28 424/422 |
| 6,136,032 A | 10/2000 | Viladot Perice et al. | |
| 6,168,631 B1 | 1/2001 | Maxwell et al. | |
| 6,419,706 B1 * | 7/2002 | Graf | A61F 2/442 623/17.16 |
| 6,764,514 B1 * | 7/2004 | Li | A61F 2/441 623/17.12 |
| 7,033,398 B2 | 4/2006 | Graham | |
| 7,069,665 B1 | 7/2006 | Adriane | |
| 7,182,783 B2 * | 2/2007 | Trieu | A61F 2/441 623/17.12 |
| 7,670,377 B2 * | 3/2010 | Zucherman | A61F 2/4425 623/17.15 |
| 7,678,153 B2 | 3/2010 | Katz et al. | |
| 7,731,753 B2 * | 6/2010 | Reo | A61F 2/442 623/17.12 |
| 8,092,547 B2 | 1/2012 | Lepow et al. | |
| 8,267,977 B2 * | 9/2012 | Roth | A61B 17/562 606/301 |
| 8,398,691 B2 | 3/2013 | Viladot Perice et al. | |
| 8,574,305 B2 * | 11/2013 | Sanders | A61F 2/4202 623/21.18 |
| 8,628,582 B2 | 1/2014 | Lavi | |
| 8,764,791 B2 | 7/2014 | Armstrong | |
| 8,974,531 B2 * | 3/2015 | de Villiers | A61F 2/4455 623/17.15 |
| 9,125,701 B2 | 9/2015 | Pech et al. | |
| 9,370,429 B1 * | 6/2016 | Sanders | A61F 2/4202 |
| 9,943,414 B2 * | 4/2018 | Werber | A61F 2/4202 |
| 2002/0128713 A1 * | 9/2002 | Ferree | A61F 2/2846 623/17.11 |
| 2003/0135214 A1 * | 7/2003 | Fetto | A61B 17/86 606/301 |
| 2004/0249463 A1 * | 12/2004 | Bindseil | A61F 2/28 623/17.16 |
| 2005/0177165 A1 * | 8/2005 | Zang | A61B 17/562 623/21.18 |
| 2005/0177243 A1 * | 8/2005 | Lepow | A61B 17/8645 623/21.11 |
| 2005/0197711 A1 * | 9/2005 | Cachia | A61B 17/562 623/21.11 |
| 2006/0041315 A1 * | 2/2006 | Katz | A61B 17/562 623/21.11 |
| 2006/0241758 A1 * | 10/2006 | Peterman | A61B 17/562 623/17.11 |
| 2007/0118218 A1 * | 5/2007 | Hooper | A61B 17/562 623/14.12 |
| 2007/0142920 A1 * | 6/2007 | Niemi | A61B 17/562 623/21.19 |
| 2007/0173954 A1 * | 7/2007 | Lavi | A61B 17/562 623/21.11 |
| 2008/0039954 A1 | 2/2008 | Long et al. | |
| 2008/0208349 A1 * | 8/2008 | Graser | A61F 2/4202 623/21.18 |
| 2008/0255664 A1 * | 10/2008 | Hogendijk | A61B 17/562 623/11.11 |
| 2009/0082818 A1 * | 3/2009 | Roth | A61B 17/562 606/304 |
| 2009/0099664 A1 * | 4/2009 | Forrester | A61B 17/562 623/21.18 |
| 2010/0023127 A1 * | 1/2010 | Shohat | A61B 17/562 623/14.12 |
| 2010/0292798 A1 * | 11/2010 | Maestretti | A61F 2/441 623/17.12 |
| 2012/0191208 A1 * | 7/2012 | Olson | A61B 17/8605 623/21.18 |
| 2013/0204386 A1 * | 8/2013 | Sanders | A61F 2/4202 623/21.18 |
| 2013/0304224 A1 * | 11/2013 | Schmidt | A61F 2/4202 623/21.18 |
| 2014/0005793 A1 | 1/2014 | Koford et al. | |
| 2014/0128974 A1 * | 5/2014 | Bromer | A61F 2/30 623/14.12 |
| 2015/0051706 A1 * | 2/2015 | Schon | A61F 2/4202 623/21.18 |
| 2017/0056190 A1 * | 3/2017 | Guilford | A61F 2/4202 |
| 2017/0143511 A1 * | 5/2017 | Cachia | A61F 2/4606 |
| 2017/0156876 A1 * | 6/2017 | Viladot Perice | A61F 2/4225 |
| 2017/0189197 A1 * | 7/2017 | Werber | A61F 2/4202 |
| 2017/0360577 A1 * | 12/2017 | Dacosta | A61F 2/4225 |
| 2018/0177601 A1 * | 6/2018 | Werber | A61F 2/4202 |

* cited by examiner

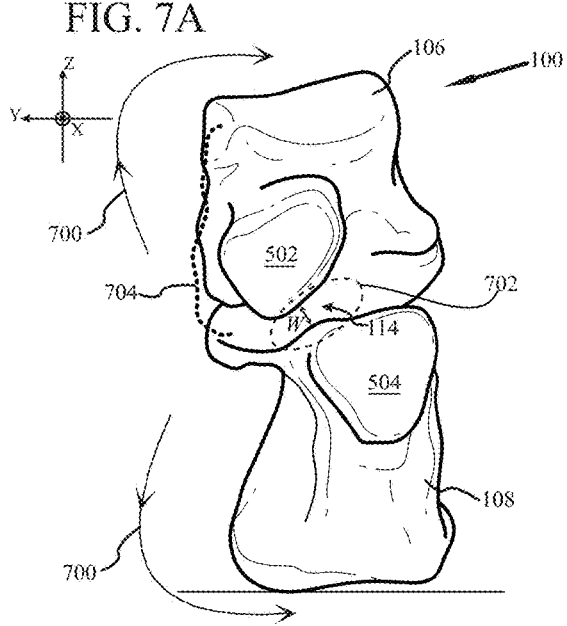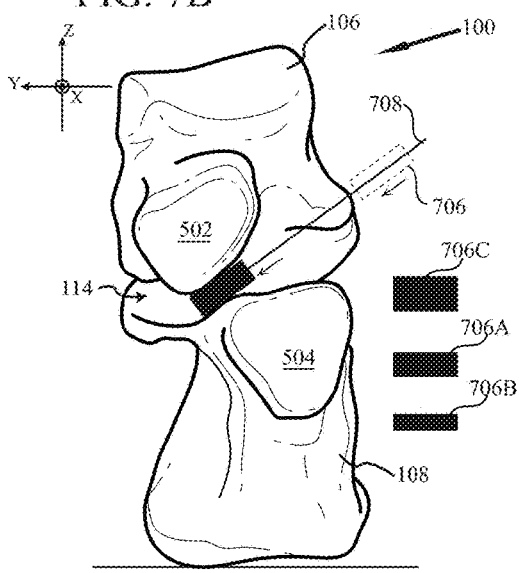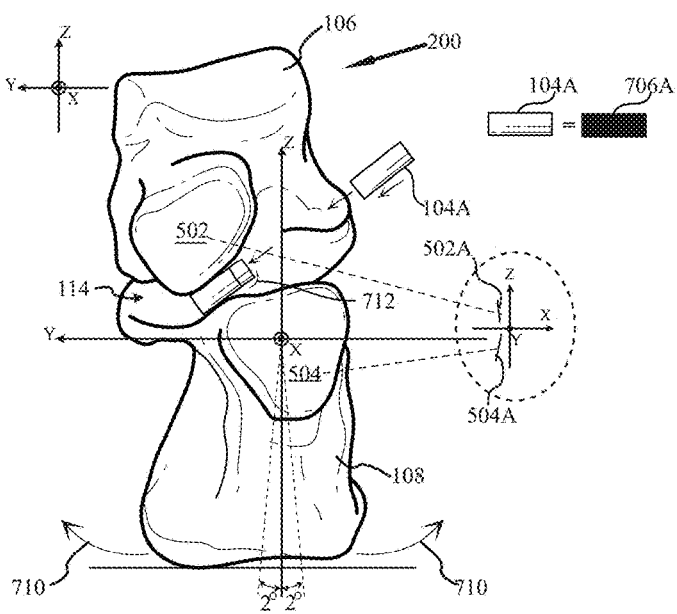

SYSTEM AND METHOD FOR NON-BINDING ALLOGRAFT SUBTALAR JOINT IMPLANT

CROSS REFERENCE TO RELATED APPLICATION

The present invention is a divisional of co-pending U.S. application Ser. No. 14/985,125 filed Dec. 30, 2015 which is incorporated herein by reference.

FIELD OF THE INVENTION

The present invention relates generally to systems and methods for a medical procedure involving an implant for the correction of skeletal misalignment, and more specifically to a non-binding allograft rod plug implant for the subtalar joint to stabilize relative alignment between the talus and calcaneus bones of the human foot.

BACKGROUND

A fallen arch or flatfoot is a deformity that affects people young and old. It is a skeletal misalignment deformity in which the arches of the foot collapse resulting in the entire sole of the foot being in complete or nearly complete contact with the ground. As there is a biomechanical relationship between the foot and lower leg, problematic issues in the inner workings of the foot structure adversely affect the rest of the body.

In proper operation the structure of a healthy arch provides an elastic connection between the hind foot and forefoot which serves to safeguard the body during weight bearing activities by displacing the impact force before it reaches the leg bones. For persons afflicted with one or both feet suffering from a flat foot condition, this elastic absorption of the foot is diminished, if not entirely non-existent. Moreover, in addition to being painful, pathologic flatfeet may cause bunions, hammertoes, heel spurs, arch pain, growing pains, shin splints, knee pain, and back pain.

Of the many bones within the human foot, the flatfoot condition is clearly evidenced by the head of the talus bone being displaced medially and distally from the navicular bone, which in turn causes lateral misalignment throughout the foot as the talus and navicular tend to move outward. In addition, there is a change in relative alignment in the subtalar joint that occurs at the meeting point between the talus bone and the calcaneus bone such that the canal which should naturally occur between them is depressed. This canal is commonly referred to as the sinus tarsi.

The subtalar joint has a neutral position where there are neutral forces passing through the multiple axis and planes that make up and permit the natural triplanar motion of the joint. When the subtalar joint's relaxed position is no longer in the intended neutral position, then the translation of forces placed on the surrounding joints, ligaments and osseous structures is abnormal. Simply put, the misalignment of the talus and calcaneus bones further imposes misalignment on other foot bones.

It has been discovered that by re-establishing the relative alignment between the talus and calcaneus bones, the overall arch structure of the foot can be reestablished as well. While this can be demonstrated by physically manipulating a person's foot, such physical manipulation is impractical during a normal use of the foot. As such there have been various efforts made to provide implants which operate to physically reposition and realign the talus and calcaneus bones.

Various implants have been developed of varying shapes and materials, such as Titanium, stainless steel, silicone, polyethylene and PEEK. The goal of such implants is to stabilize the talus and calcaneus bones with respect to each other without fusing them. While perhaps effective at reestablishing an improved alignment of the talus and calcaneus bones the options for implants known to date fall short of truly reestablishing the triplanar motion and naturally gliding motion of the subtalar joint.

One such effort is set forth in the prior art reference of Maxwell U.S. Pat. No. 6,168,631 teaching a Subtalar Implant System and Method for Insertion and Removal. Maxwell specifically teaches an implant sized and shaped to fit within the sinus tarsi, and that the implant has exterior threads so as to engage the tissues, i.e. bones, of the sinus tarsi. Maxwell also teaches that the implant is preferably made from a titanium based alloy as Maxwell asserts that it is an object of the invention not to deform under post operative compressive forces. While perhaps effective in re-establishing spacing between the talus and calcaneus bones, as the Maxwell implant is quite literally screwed in-between them, the screwing nature also binds them and substantially eliminates the natural triplanar motion of the subtalar joint. In addition, the metal nature of the Maxwell implant results in the patient experiencing a hard stop—the foot simply does not move in some directions and the resistance to compression can be painful. In addition, over time and as a result of repeated use of the repaired foot, the Maxwell implant may actually abrade, or cause the surrounding bone tissues to abrade—leading to shards of foreign or natural material within the subtalar joint further causing pain and perhaps requiring surgical extraction of the debris, and/or the Maxwell implant itself as suggested by the title.

The prior art reference of Lepow U.S. Pat. No. 8,092,547 for a Subtalar Implant Assembly teaches an implant with a core region 16 that is tapered between a first end 24 and a second end, the core region 16 further having a threaded region 18 formed on and extending outward. As with the Maxwell implant, the Lepow implant is screwed into place between the talus 38 and calcaneus 40 bones. As such, once again, this screwed in nature binds the talus and calcaneus bones and substantially eliminates the natural triplanar motion of the subtalar joint. Lepow also teaches forming the core region from various plastics, metals, metal alloys, glass, ceramics, composite materials such as carbon fiber, bioabsorbable materials, or the like and combinations of metals and/or plastics. Once again the Lepow implant is intended to be a very solid non-deformable implant. As such, the motion of the foot may be un-natural and perhaps painful for some person's, and once again shards of natural and foreign materials may develop within the subtalar joint resulting in pain and the need for surgical extraction.

The prior art reference of Graham U.S. Pat. No. 7,033,398 for a Sinus Tarsi Implant is yet another threaded implant. The Graham implant is specifically taught to have a first member 106 with an outer surface generally configured in the shape of a right conical frustrum between a second member 108 and a cylindrical third member 110, the third member 110 being sized to fit within the sinus tarsi. Preferably fashioned about the cylindrical third member 110 is a tissue engagement surface more specifically taught as one or more channels 112, which in a preferred embodiment are a continuous thread. Once again, the Graham implant is intended to be screwed into place with the one or more channels 112 of the third member 110 binding with the talus and calcaneus bones proximate to the sinus tarsi. And again, such binding likely eliminates the natural triplanar motion of the subtalar joint. The Graham implant is also taught to be constructed of by a polymer which is substantially incompressible and tough, once again potentially resulting in an uncomfortable if not painful implant for some person's. And again, the binding nature of the Graham implant may once again result in shards of foreign or natural material within the subtalar joint.

Other threaded implant prior art references exist as well, such as Pech U.S. Pat. No. 9,125,701 and Katz U.S. Pat. No. 7,679,153. As noted in the details above, it is a clear aspect of a threaded implant to be screwed in-between the talus and calcaneus bones, so as to bind them in a restored alignment, but in tradeoff for this bound alignment the natural triplanar motion of the subtalar joint is substantially reduced if not completely eliminated. The stress and force imparted by this unnatural elimination may and often does cause abrasion of implant and or bone tissue.

The prior art reference of Rappaport U.S. Pat. No. 4,450,591 teaches an Internal Anti-Prorotary Plug Assembly and Process of Installing the Same. Rappaort departs from the threaded implant approach. As taught by Rappaport, a biocompatible plastic cone shaped plug is provided with a tie line extending from the minor base of the plug. After being inserted into the sinus tarsus or opening of the subtalar joint, the tie line is bound about the deltoid ligament to hold the cone shaped plug in place. While perhaps avoiding the bound alignment imposed by a threaded implant, the tie line may cause insult and abrasion to the tendon as compressive forces upon the conical shaped body result in the generation of lateral forces upon the plug and thereby tension the tie line. Further, the plastic may still abrade or cause the talus and calcaneus bones to abrade.

Moreover, although there are a growing number of implants and procedures which strive to alleviate some of the issues associated with flatfoot by stabilizing the subtalar joint, in the main they appear to sacrifice the natural and expected gliding motion of the joint for improved relative spacing. In addition, as this reduced natural and expected gliding motion is known to often cause abrasion, extraction and replacement of the implants appears to be an expected likelihood in the future, subjecting the patient to an additional surgical procedure as well as potential pain and discomfort when and if the implant breaks down or abrades body tissues.

Hence there is a need for a system and method that is capable of overcoming one or more of the above identified challenges.

SUMMARY OF THE INVENTION

Our invention solves the problems of the prior art by providing novel systems and methods for a non-binding allograft subtalar joint implant.

In particular, and by way of example only, according to one embodiment of the present invention, provided is a method to provide a non-binding allograft subtalar joint implant into a person's foot proximate to the ankle including: surgically accessing a canal within a person's foot proximate to the person's talus and calcaneus bones, the canal having a width between the talus and calcaneus bones; selecting a pre-formed allograft rod plug having a diameter of about the canal width, the pre-formed allograft rod plug being resiliently compressible and flexible; disposing the selected pre-formed allograft rod plug snuggly within the canal and adjacent to the talus and calcaneus bones, the pre-formed rod plug stabilizing a relative alignment between the talus and calcaneus bones while permitting relative sliding between the talus and calcaneus; evaluating a range of motion of the foot; in response to an abnormal range of motion, removing the pre-formed allograft rod plug and trimming at least a portion of the pre-formed allograft rod plug and redisposing the trimmed pre-formed allograft rod plug within the canal to re-evaluate the range of motion; and in response to a normal range of motion, surgically closing access to the canal.

For another embodiment, provided is a method to provide a non-binding allograft subtalar implant into a person's foot proximate to the ankle including: surgically accessing a sinus tarsi within a person's foot proximate to the person's talus and calcaneus bones; extracting a fatty tissue plug from the sinus tarsi; determining a maximum width within the canal between the talus and calcaneus bones; selecting a pre-formed allograft rod plug having a diameter of about an equivalent size to the determined maximum width, the pre-formed allograft rod plug being resiliently compressible and flexible; disposing the selected pre-formed allograft rod plug snuggly within the sinus tarsi and adjacent to the talus and calcaneus bones, the pre-formed rod plug stabilizing a relative alignment between the talus and calcaneus bones while permitting relative sliding between the talus and calcaneus bones; evaluating a range of motion of the foot; in response to an abnormal range of motion, removing the pre-formed allograft rod plug and in a first instance trimming at least a portion of the pre-formed allograft rod plug and redisposing the trimmed pre-formed allograft rod plug snuggly within the sinus tarsi to re-evaluate the range of motion, and in a second instance selecting a second pre-formed allograft rod plug having a different diameter size and disposing the second pre-formed allograft rod plug snuggly within the sinus tarsi to re-evaluate the range of motion; and in response to a normal range of motion, surgically closing access to the sinus tarsi.

Further, in yet another embodiment, provided is a method to provide a non-binding allograft subtalar implant for implant into a person's foot proximate to the ankle including: harvesting at least one reticular dermis element from at least one donor; processing the reticular dermis element to remove cellular component and leave extracellular matrix and scaffold, and drying the reticular dermis element; rolling the processed reticular dermis element into a rod having a diameter about equal to an average width of a canal between a person's talus and calcaneus bones, the pre-formed allograft rod plug being resiliently compressible and flexible; cutting the rod into pre-determined lengths; freeze drying each cut length; and packaging each freeze dried cut length; wherein when unpacked and snuggly disposed between the person's talus and calcaneus bones, the pre-formed allograft rod plug compresses during normal use of the person's foot and maintains the canal in an anatomically correct alignment and reduces a tendency for abnormal motion between the person's talus and calcaneus bones.

Further still, in yet another embodiment provided is a system to provide a non-binding allograft subtalar joint implant into a person's foot proximate to the ankle including: at least one sterile pre-formed allograft rod plug having a diameter about equal to an average width of a canal between a person's talus and calcaneus bones, the pre-formed allograft rod plug being resiliently compressible and flexible; wherein when snuggly disposed between the person's talus and calcaneus bones, the pre-formed allograft rod plug compresses during normal use of the person's foot and maintains the canal in an anatomically correct alignment and reduces a tendency for abnormal motion between the person's talus and calcaneus bones.

BRIEF DESCRIPTION OF THE DRAWINGS AND SUPPORTING MATERIALS

FIGS. 7A-7C are side cut through views of the bone structure of the human foot shown in FIG. 2 and a plurality of non-binding allograft subtalar joint implants for reconstructing the foot in accordance with at least one embodiment of the present invention;

Figure 10A:
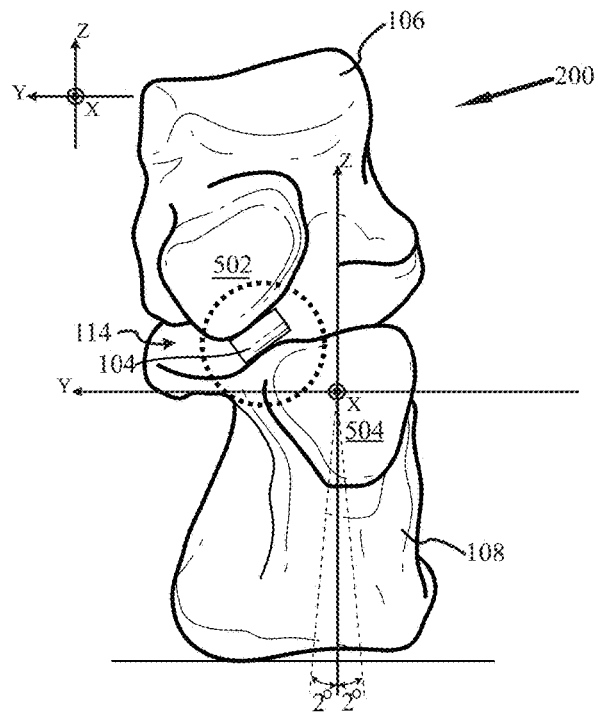
Figure 10B:
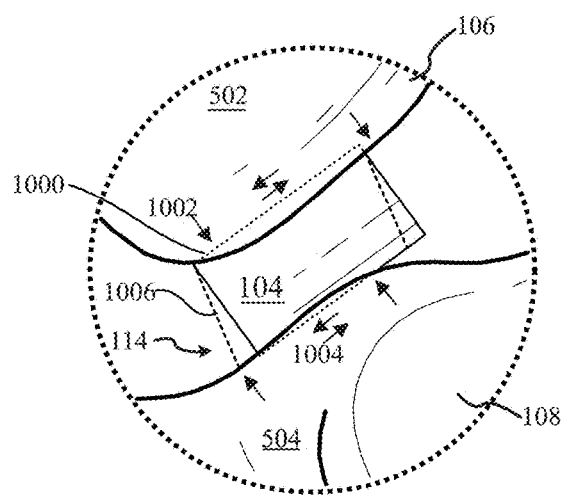
Figure 11:
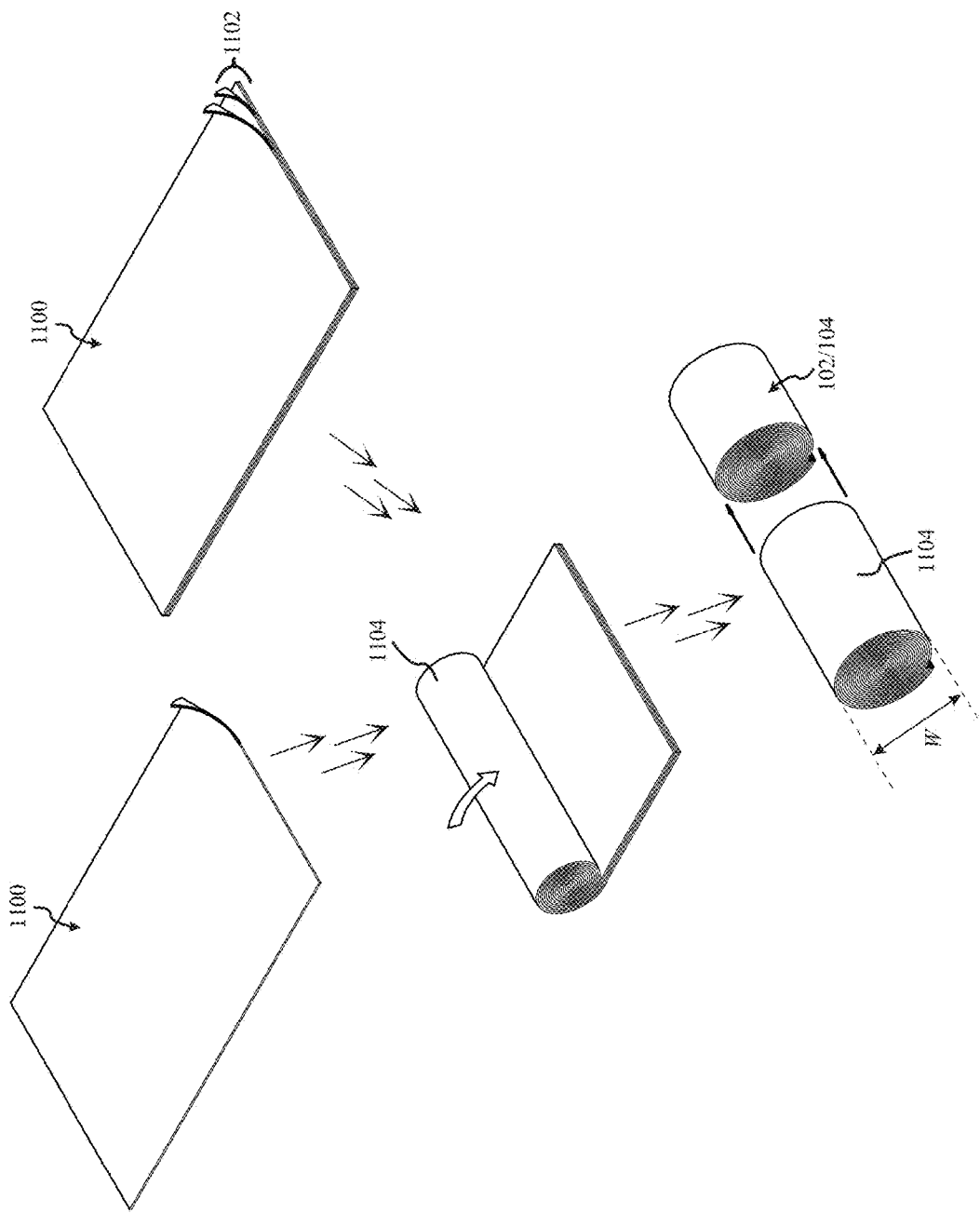

FIGS. 10A and 10B illustrate a side view and enlarged partial view similar to FIG. 7C, further illustrating the non-binding allograft subtalar joint implant permitting compression and relative sliding in accordance with at least one embodiment of the present invention; and FIG. 11 illustrates the process of making at least one non-binding allograft subtalar joint implant, such as preformed allograft rod plug in accordance with at least one embodiment of the present invention.

DETAILED DESCRIPTION

Our invention solves the problems of the prior art by providing novel systems and methods for a non-binding allograft subtalar joint implant Before proceeding with the detailed description, it is to be appreciated that the present teaching is by way of example only, not by limitation. The concepts herein are not limited to use or application with a specific system or method for a non-binding allograft subtalar joint implant. Thus, although the instrumentalities described herein are for the convenience of explanation shown and described with respect to exemplary embodiments, it will be understood and appreciated that the principles herein may be applied equally in other types of systems and methods involving or pertaining to a non-binding allograft subtalar joint implant.

This invention is described with respect to preferred embodiments in the following description with reference to the Figures, in which like numbers represent the same or similar elements. Further, with the respect to the numbering of the same or similar elements, it will be appreciated that the leading values identify the Figure in which the element is first identified and described, e.g., element 100 appears in FIG. 1.

Figure 1:
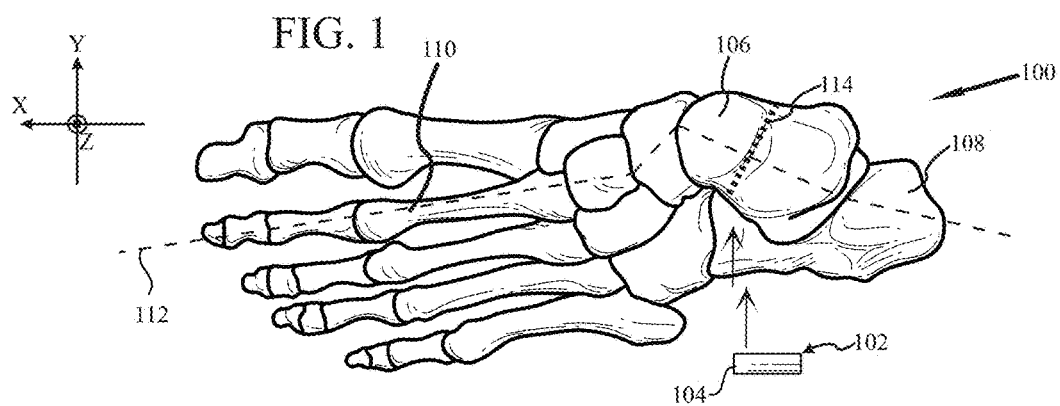
FIG. 1 illustrates a top view of the bone structure of a human foot exhibiting flat foot and a non-binding allograft subtalar joint implant for reconstructing the foot in accordance with at least one embodiment of the present invention.

Turning now to FIG. 1, presented is a top skeletal view of a person's foot 100 exhibiting flatfoot condition before the corrective measure of implanting the non-binding allograft subtalar implant 102. An allograft is tissue harvested from one person for surgical transplant to another person. The use of allograft tissue dates back over one hundred and fifty years, and unlike synthetic and metal implants their origin as human tissue permits them to be advantageously incorporated by the receiving body. It should be noted that the Allograft subtalar implant 102 is not bone, for a bone implant would likely fuse with the bones of the subtalar joint, which for the purposes of reconstruction for normal operation of the subtalar joint is not necessarily desired.

Rather, for at least one embodiment the allograft subtalar implant 102 is formed generally from acellular dermis tissue which has been processed so as to be substantially inert, and while compacted to a density sufficient to restore about a natural alignment between the talus 106 and calcaneus 108 bones, it is also resiliently compressible. As such the allograft subtalar implant 102 advantageously provides both reconstructive support and about natural motion during foot use.

Indeed as the allograft subtalar implant 102 is provided by harvested human tissue that has been processed to an acellular state, it will almost certainly and advantageously be accepted by the receiving body. More specifically, the inert structure of the allograft subtalar implant 102 permitting if not promoting the growth of new tissue which over time will incorporate it as a part of the receiving body.

As will be further appreciated, for at least one embodiment the non-binding allograft subtalar implant is a preformed allograft rod plug, hereinafter ARP 104. Moreover the ARP 104 has a diameter of about the diameter of a normal canal within a person's foot proximate to the talus 106 and calcaneus 108 bones.

To briefly summarize, for at least one embodiment provided is a non-binding allograft subtalar joint implant 102 for surgical implant into a person's foot 100 proximate to the ankle. This system for this repair includes at least one sterile ARP 104 having a diameter about equal to an average width of a canal between a person's talus 106 and calcaneus bones 106, the ARP 104 being resiliently compressible and flexible. When snuggly disposed between the person's talus 106 and calcaneus 108 bones, the ARP 104 compresses and resiliently expands back during normal use of the person's foot and maintains the canal in an anatomically correct alignment and reduces a tendency for abnormal motion between the person's talus 106 and calcaneus 108 bones.

Advantageously, and as will be further appreciated with the following description, the ARP 104 is non-binding to the talus 106 and calcaneus 108 bones, being held in place by the resilient nature of the ARP 104. Indeed this lack of anchoring by threads or grooves caused to bite into the talus 106 and calcaneus 108 bones permits the ARP 104 to stabilize the relative alignment between the talus 106 and calcaneus 108 bones while permitting relative sliding between the talus 106 and calcaneus 108. Indeed, as used herein, the term "snuggly" as used to describe the fit of ARP 104 within the canal, is understood and appreciated to convey the understanding that it is a tight but comfortable fit, permitting some movement without anchoring or binding the talus 106 and calcaneus 108 in a substantially ridged alignment.

To facilitate the description of systems and methods for this non-binding allograft subtalar joint implant, or ARP 104, the orientation of the foot and ARP 104 as presented in the figures are referenced to the coordinate system with three axis orthogonal to one another as shown in FIG. 1. The axis intersect mutually at the origin of the coordinate system, which is chosen to be the center of the person's foot, however the axes shown in all figures are offset from their actual locations for clarity and ease of illustration.

In a normal healthy foot, a longitudinal midline may be viewed running through at least the second metatarsal 110, the talus 106 and the calcaneus 108. However in the flatfoot conceptualized by FIG. 1, this longitudinal midline is distorted, as shown by dotted line 112. Indeed, as shown in FIG. 1 the head of the talus 106 is disposed away from the second metatarsal 110 so as to even protrude along the inside edge of the person's foot.

Moreover, for the flatfoot condition, the misalignment of the bones in the subtalar joint, and most specifically the talus 106 and calcaneus 108, results in a significant displacement of the bones and frustrates the longitudinal axis 112. The canal within the foot 100 defined by the talus 106 and calcaneus 108 is impinged as well, such that for FIG. 1, it is shown merely as a dotted line 114. This canal 114 or cylindrical cavity as it may also be described is often referred to as the sinus tarsi.

Figure 2:
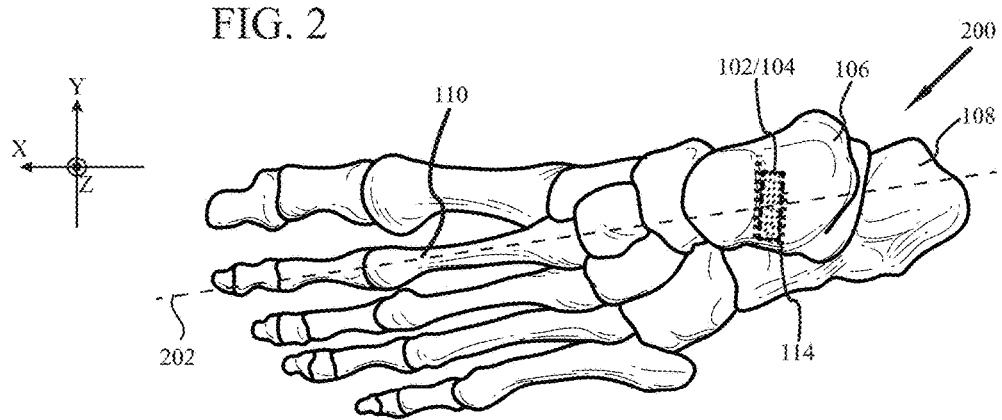
FIG. 2 illustrates top view of the bone structure of a human foot reconstructed with the a non-binding allograft subtalar joint implant in accordance with at least one embodiment of the present invention.

The flatfoot condition can be repaired. As shown in FIG. 2, with the ARP 104 snuggly disposed within the canal 114 such that the canal 114 is spread back substantially to about a normal width, the alignment of the talus 106 and calcaneus 108 is vastly corrected to approach, if not reestablish, a normal alignment, providing repaired foot 200. In contrast to FIG. 1, in FIG. 2 the longitudinal axis 202 through the second metatarsal 110, the talus 106 and calcaneus 108 is now normal, for repaired foot 200.

Figure 3:
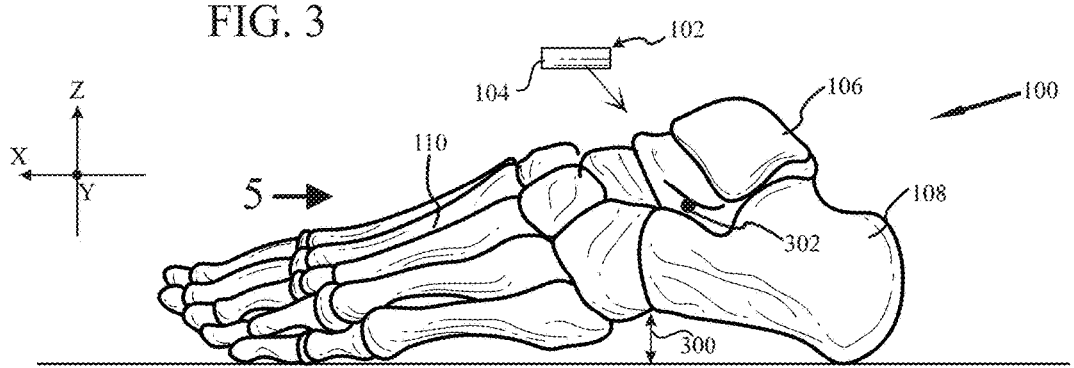
FIG. 3 illustrates a side view of the bone structure of the human foot shown in FIG. 1 exhibiting flat foot and a non-binding allograft subtalar joint implant for reconstructing the foot in accordance with at least one embodiment of the present invention.

FIG. 3 is a side view corresponding to FIG. 1 of foot 100 in the initial flatfoot condition. As with FIG. 1 the alignment of the bones is distorted and the arch 300 of the foot 100 is substantially non-existent. In addition, the talus 106 and calcaneus 108 are so misaligned that the canal 114 between them is not even radially apparent, shown merely as a conceptual dot 302. FIG. 3 also illustrates the line-of-sight view "5" for FIG. 5 below conceptualizing a cross-section view proximate to the canal 114 of foot 100 before repair.

Figure 4:
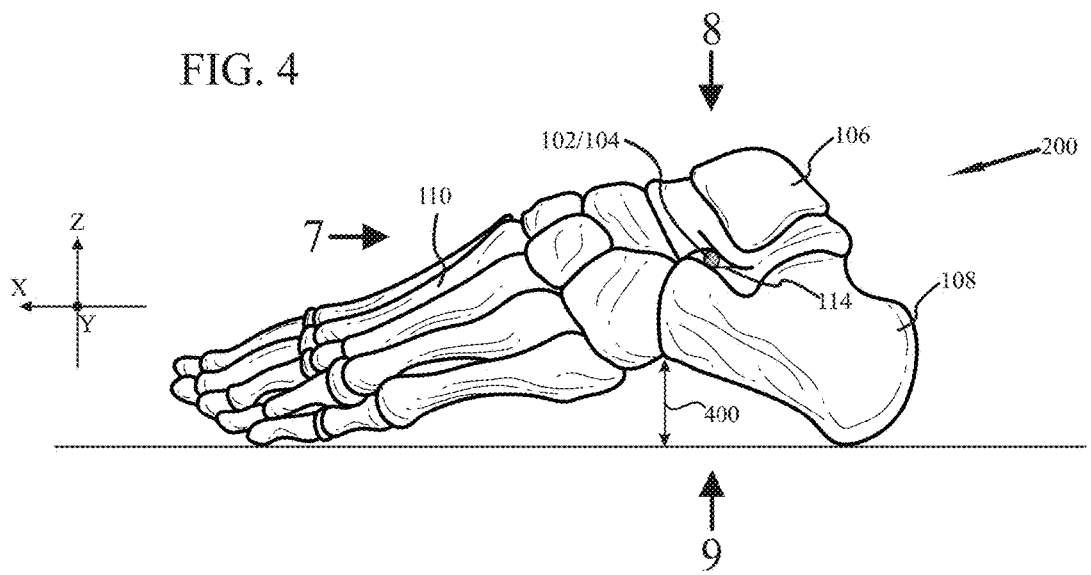
FIG. 4 illustrates side view of the bone structure of the reconstructed human foot shown in FIG. 2 with the a non-binding allograft subtalar joint implant in accordance with at least one embodiment of the present invention.

FIG. 4 is a side view of repaired foot 200 shown in FIG. 2. As shown, ARP 104 is snuggly disposed within the canal 114. A visual comparison with FIG. 3 helps further demonstrate how reestablishing the canal 114, by lifting the talus 106 away from the calcaneus 108 effectively lifts the entire bone structure of the repaired foot 200. Indeed raising the head of the talus 106 acts as a lever arm and pulls upon the tendons of the foot to naturally realign a plurality of bone elements within repaired foot 200.

As shown, repaired foot 200 has a substantially normal arch 400. As with FIG. 3, FIG. 4 also illustrates the line-of-sight views "7", "8" and "9" for FIGS. 7, 8 and 9 respectively.

Figure 5:
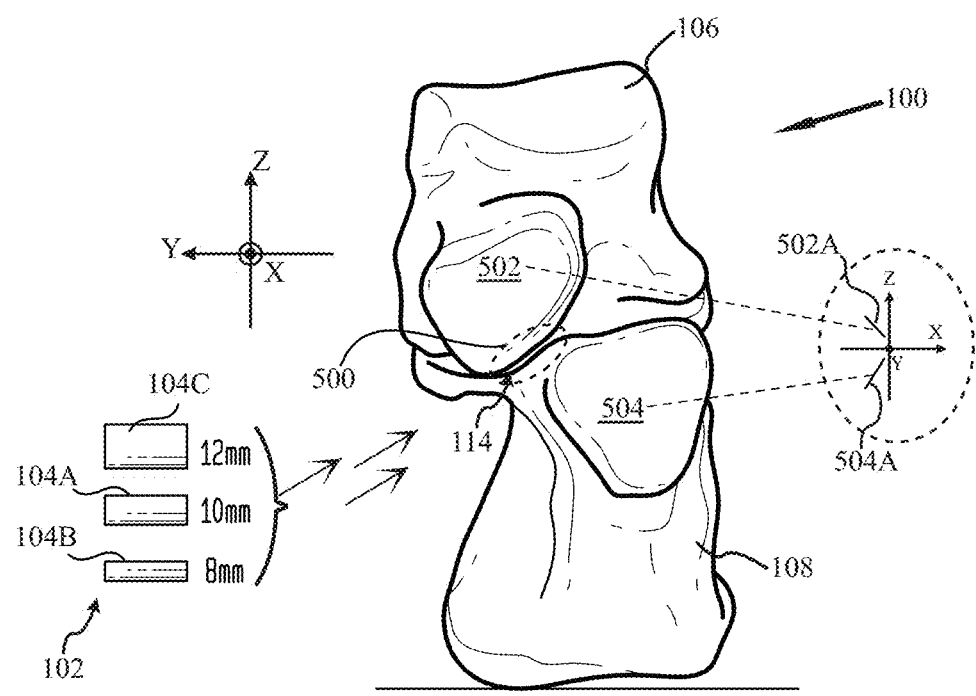
FIG. 5 illustrates a side cut through view of the bone structure of the human foot shown in FIG. 1 and a plurality of non-binding allograft subtalar joint implants for reconstructing the foot in accordance with at least one embodiment of the present invention.

FIG. 5 as noted above is a cross-section view of foot 100 before repair. In this view, the misalignment of the talus 106 and the calcaneus 108 is more fully appreciated. Indeed the canal 114, and more specifically the region within dotted oval 500 is substantially compressed together. In addition, the relative improper angles of the head 502 of the talus 106 and the head 504 of the calcaneus 108 are shown with side view surface angle representations 502A and 504A respectively.

Also shown in FIG. 5 are ARP 104A having a length that is longer than the average sinus tarsi and a diameter of about the average width of a normal sinus tarsi, ARP 104B having a length that is longer than the average sinus tarsi and a diameter smaller then the average width of a normal sinus tarsi, and ARP 104C having a length that is longer than the average sinus tarsi and a diameter larger then the average width of a normal sinus tarsi. Moreover, a selection of different ARP 104 implants eases the ability of the surgeon performing the repair to select an ARP 104 which will most closely approximate the width of the sinus tarsi in the person's foot being reconstructed.

More specifically, for at least one embodiment, ARP 104A has a length of about 25 mm and a diameter of about 10 mm, ARP 104B has a length of about 25 MM and a diameter of about 8 mm, and ARP 104C has a length of about 25 mm and a diameter of about 12 mm. Of course in varying embodiments ARP 104 implants having alternative diameters, and/or even different lengths, may be provided.

As has also been shown by way of illustration, in initial state, each ARP 104 implant has a generally consistent diameter. It should also be understood and appreciated that each ARP 104 implant is also resiliently compressible and flexible. Moreover, as will be further discussed below, each ARP 104 is not a ridged element and is not constructed with anchoring elements such as screw threading, channeling or tether.

Indeed as each ARP 104 is slightly compressible, it is the resilient nature of the ARP 104 that permits it to be disposed within the sinus tarsi 114 adjacent to the talus 106 and calcaneus 108 so as to maintain the sinus tarsi 114 in about a normal open state and stabilize the relative alignment between the talus 106 and calcaneus 108 while permitting relative sliding between the talus 106 and calcaneus 108. Moreover, the resilient nature of the ARP 104 permits it to advantageously remain in a snug position within the canal 114 while advantageously also permitting natural movement of the talus 106 and calcaneus 108 that is not otherwise achieved with a more traditional anchoring implant that is screwed, bound or otherwise affixed in place by a surgeon or other repairing technician.

For at least one embodiment, the method of providing a non-binding allograft subtalar implant into a person's foot proximate to the ankle may be summarized as follows. Surgically accessing a canal 114 within a person's foot proximate to the person's talus 106 and calcaneus 108 bones and determining a maximum width within the canal between the talus 106 and calcaneus 108 bones. With the maximum width determined, selecting an ARP 104 having a diameter of about an equivalent size to the determined maximum width, the pre ARP 104 being resiliently compressible and flexible. The selected ARP 104 is then snuggly disposed within the canal and adjacent to the talus 106 and calcaneus 108 bones, the ARP 104 stabilizing a relative alignment between the talus 106 and calcaneus 108 bones while permitting relative sliding between the talus 106 and calcaneus 108. The range of motion of the foot is then evaluated. In response to an abnormal range of motion the disposed ARP 104 is removed. In a first instance, a portion is trimmed and the trimmed ARP 104 is redisposing snuggly within the canal 114 to re-evaluate the range of motion. In a second instance a second ARP 104 is selected having a different diameter size. This second ARP 104 is then snuggly disposed within the canal to re-evaluate the range of motion. In response to a normal range of motion, surgically closing access to the canal.

Figure 6:
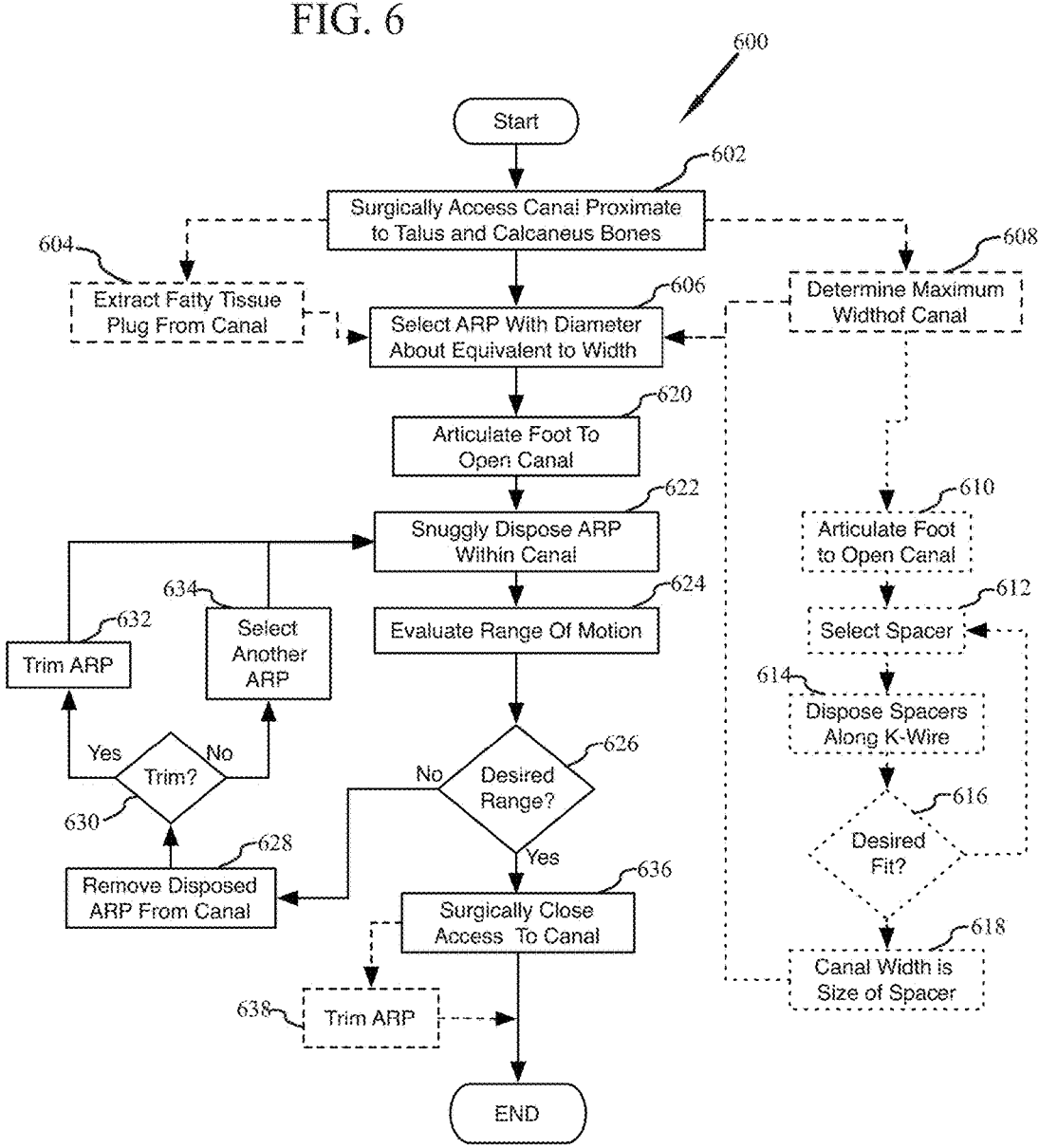
FIG. 6 is a high level flow diagram for a method of providing a non-binding allograft subtalar join implant into a person's foot proximate to the ankle in accordance with at least one embodiment of the present invention.

Methods of repair are perhaps more fully appreciated with respect to an exemplary method 600 shown in FIG. 6 in connection with at least FIGS. 7A and 7B. It is also to be understood and appreciated the described method need not be performed in the order in which it is herein described but that this description is merely exemplary of at least one method for advantageously providing a non-binding allograft subtalar implant into a person's foot proximate to the ankle.

In general, as shown in FIG. 6, method 600 commences by surgically accessing the canal 114 proximate to the talus 106 and calcaneus 108 bones, block 602. It is very common for a fatty tissue plug to be naturally occurring within the canal 114, which may optionally be removed, optional block 604.

With the canal 114 now exposed, it is appropriate to select an ARP 104 with a diameter about equal to the width of the canal, block 606. For at least one embodiment, the surgeon may start by selecting an ARP 104 having a diameter that is about equivalent to the average width of the canal 114 in an average person.

An improved selection of an ARP 104 may be facilitated by determining the maximum width of the canal 114 for the current patient, block 608. For at least one embodiment, this determination of maximum width is optionally achieved through the use of sizers/spacers which correlate in size to various ARP 104 implant options.

More specifically, as was discussed above with respect to FIG. 5, the canal in the flatfooted patient is likely substantially collapsed. Accordingly, the surgeon or other operating assistant may articulate the person's foot so as to open the canal 114, optional block 610.

In FIG. 7A the foot 100 has been manipulated, as indicated by arrows 700, so as to realign the talus 106 and calcaneus 108 in about a normal orientation. This manipulation serves to also open the canal region shown within dotted circle 702, and more specifically the sinus tarsi 114. The dotted side line 702 in FIG. 7A represents the original position of the talus 106 as shown in FIG. 5. In addition, the sinus tarsi 114 is shown now open and having a maximum width W.

As shown in FIG. 7B, this width W of the sinus tarsi 114 may be measured through the use of one or more spacer 706, such as spacers 706A, 706B and 706C which correlate in diameter to the implants ARP 104A, ARP 104B and ARP 104C. For at least one embodiment, each spacer 706 is a blunt trocar which may be introduced to the sinus tarsi 114 along a Kircshner wire 708, such as a 0.062 inch Kircshner wire serving as a guide wire. More specifically, for at least one embodiment, each spacer 706 is introduced to the sinus tarsi 114 through a cannula (not shown) and pushed into place with a trocar. Following the spacing evaluation the spacer 706 is extracted. The Kircshner wire serves as an additional guide for this process. Of course in varying embodiments, the surgeon may use other instrumentation to position and remove each spacer 706.

Moreover, with respect to FIG. 7B, spacer 706A is selected, optional block 612, and disposed to the canal 114 along a Kircshner wire, optional block 708. The surgeon then evaluates the fit of the spacer, optional decision 616. If it is too big or too small, the surgeon then selects an alternative spacer, optional block 612 and repeats the process. When the fit is as desired, optional decision 616, the width W of the sinus tarsi canal 114 is known to be the diameter of the current spacer 706, optional block 618. With this determined width W, the surgeon then selects an ARP 104 with a diameter about equivalent to the space, block 606.

Having selected an ARP 104 of an appropriate size, if the foot is not properly articulated to open the canal, the surgeon now does so, block 620. Method 600 proceeds with the ARP 104 being snuggly disposed within the sinus tarsi 114 as shown in FIG. 7C. More specifically, the ARP 104 is disposed snuggly within the narrow region of the sinus tarsi canal 114 such that the ARP 104 is in compressive contact with both the tarsi 106 and calcaneus 108. Indeed the ARP 104 may be disposed in direct contact with actual bone tissue of the tarsi 106 and calcaneus 108, or in direct contact with one or more tissues covering the bone tissue of the tarsi 106 and calcaneus 108. For at least one embodiment, the ARP 104 is pre-trimmed prior to being snuggly disposed within the sinus tarsi 114. As with the placement of one or more spacers 706, a cannula (not shown) and trocar may be used to position and snuggly dispose ARP 104 within the sinus tarsi canal 114.

With the ARP 104 now disposed, the range of motion of the foot 100 s evaluated, block 622. This range of motion of the foot 100, and more specifically the subtalar joint is performed by rotating the foot 100 from side to side about the X-Axis as shown in FIG. 7B by arrows 710. In a normal foot, this range of side to side motion is typically no more than 4 degree to either side of normal, and more preferably no more than 2 degrees to either side of normal. More specifically, for at least one embodiment an evaluation of rotation motion is performed to confirm no more than 2 degrees of inverted rotation and no more than 2 degrees of everted rotation. Accordingly, for at least one embodiment, the surgeon articulates the calcaneus 108 and checks for more than 2 degrees of motion from side to side.

If the disposed ARP 104 does not permit the proper range—either too much or too little, decision 626, the disposed ARP 104 is removed from the canal 114, block 628. For at least one embodiment, method 600 proceeds with an evaluation of whether to trip the ARP 104 or select another ARP 104 having a different diameter, decision 630.

In a first instance, the decision is to trim the ARP 104, block 632 and then snuggly dispose the trimmed ARP 104 within the canal 114, block 622. In a second instance, the decision is to select a second ARP 104 having a different diameter size, block 634 and then dispose the second ARP 104 within the canal 114, block 622. Following the trimming or selection of a replacement ARP 104, the evaluation of motion is performed once again, block 624, and the process of trimming or reselecting repeated if necessary.

When the range of motion is in the desired range, decision 626, the alignment of the tarsi 106 and calcaneus 108 is understood to be corrected. Now, the relative proper angles of the head 502 of the talus 106 and the head 504 of the calcaneus 108 for repaired foot 200 are shown with side view surface angle representations 502A' and 504A' respectively.

The surgeon then proceeds to surgically close access to the canal 114, block 636. Of course, in this closing process, the surgeon may also optionally trim the excess 712 of ARP 104 which may extend from the canal 114, optional block 638.

Figure 8:
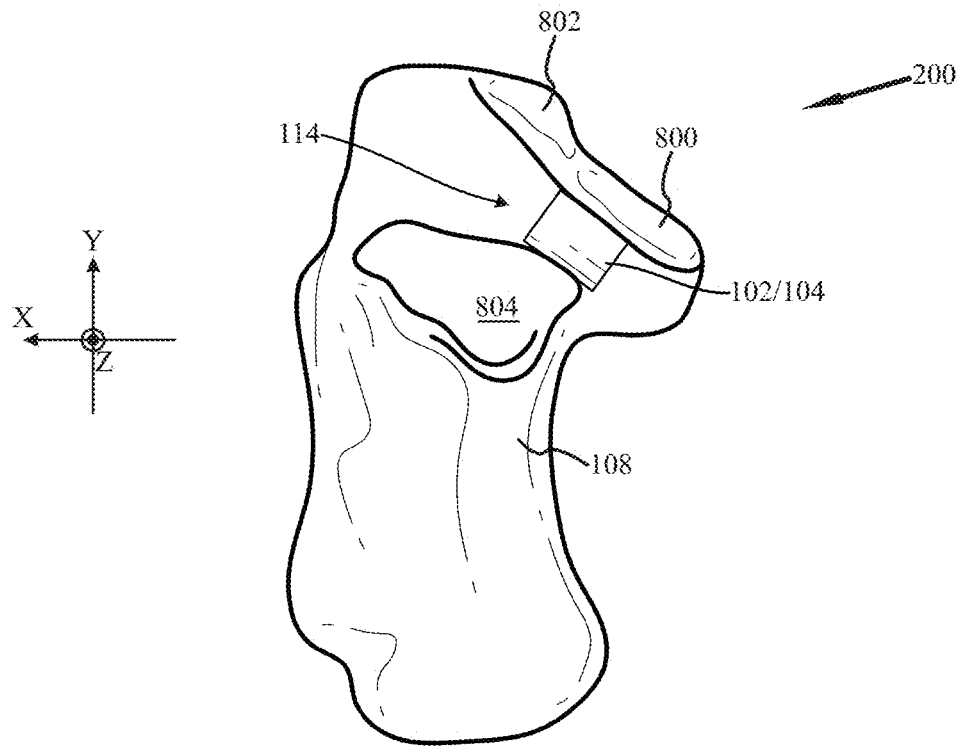
FIG. 8 illustrates partial top view of the bone structure of a human foot reconstructed with the a non-binding allograft subtalar joint implant shown in FIG. 2 in accordance with at least one embodiment of the present invention.

FIG. 8 presents the ARP 104 snuggly disposed within the sinus tarsi 114 as viewed from above, generally along the line of sight 8 as suggested in FIG. 4., i.e. a top view. Shown are features of the calcaneus 108 that define the bottom half of the sinus tarsi 112. In this view, the sinus tarsi 114 is posterior to (as in behind) the middle 800 and anterior talar facet 802 of the calcaneus 108. The sinus tarsi 114 is anterior to (as in front of) the subtalar joint provided in part by the posterior talar facet 804 of the calcaneus 104.

Figure 9:
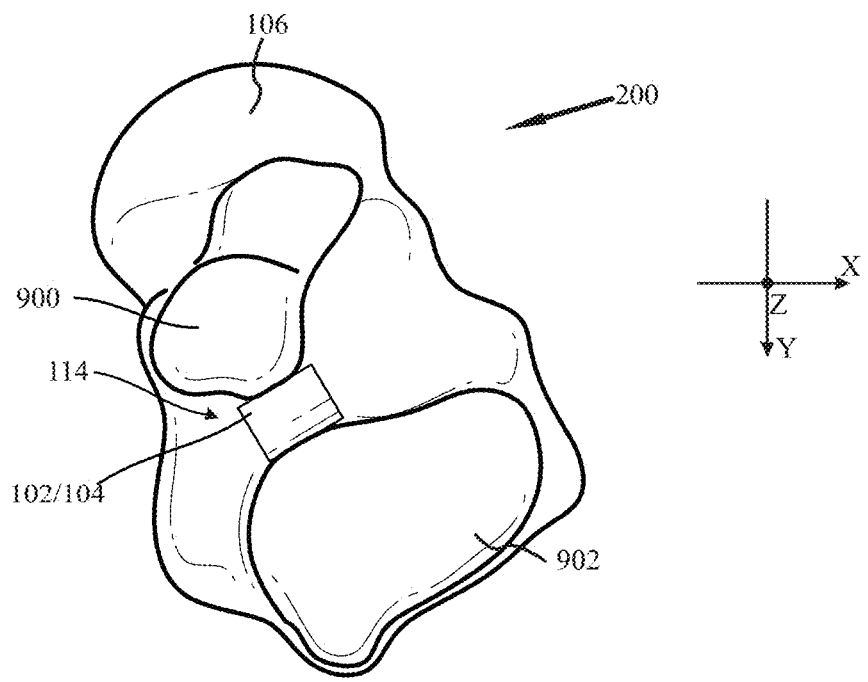
FIG. 9 illustrates partial top bottom of the bone structure of a human foot reconstructed with the a non-binding allograft subtalar joint implant shown in FIG. 2 in accordance with at least one embodiment of the present invention.

FIG. 9 presents the ARP 104 snuggly disposed within the sinus tarsi 114 as viewed from below, generally along the line of sight 9 as suggested in FIG. 4, i.e., a bottom view. Shown are the features of the talus 106 that define the top half of the sinus tarsi 114 in complement to those features shown in FIG. 9. Specifically, the sinus tarsi 114 is shown posterior to (as in behind) the talocalcaneonavicular joint which comprises the middle 900 and anterior calcaneal facet of the talus 106. The sinus tarsi 114 is anterior to (as in front of) the subtalar joint provided in part by the posterior calcaneal facet 902 of the talus 106.

Moreover, as shown in FIG. 10A, presenting substantially the same view as FIG. 7C of repaired foot 200, snuggly disposed, ARP 104 now maintains the sinus tarsi 114 in an anatomically correct alignment and reduces a tendency for abnormal motion between the person's talus 106 and calcaneus 108. In addition, as shown in the enlarged section of FIG. 10B, the ARP 104 advantageously compresses (shown by force arrows 1002) the during normal use of the person's repaired foot 200, shown by dotted lines 1000 indicating the original uncompressed sidewall of ARP 104. Further still, ARP 104 can advantageously distort laterally as well in response to relative sliding motions, shown by arrow sliding arrows 1004, during the normal use of the person's repaired foot 200, shown by dotted lines 1006 indicating potential end distortion as the talus 106 and calcaneus 108 move relative to each other.

Moreover, ARP 104 provides the anatomical lifting of the talus 106 relative to the calcaneus 108 as other implants strive to achieve, but the ARP 104 is advantageously distinct in not being anchored by artificial means such as threads, grooves or ties. The ARP 104 therefore permits partial compression from loading 1002 during use of the foot while still achieving the leverage based realignment of the talus 102 and relative sliding 1004 and/or gliding between the talus 106 and calcaneus 108 as is found in a healthy foot.

The advantages of the ARP 104 are achieved by the nature of the ARP 104. Specifically, for at least one embodiment ARP 104 is provided by a rod of acellular dermis. Dermis is a layer of skin between the epidermis and subcutaneous tissues. The dermis is divided into two layers, the superficial area adjacent to the epidermis called the papillary region and a deep thicker area known as reticular dermis. Structural components of the dermis are collagen, elastic fibers and extrafibrillar matrix.

Constructed as a rod, and more specifically a rolled rod, ARP 104 provides excellent compressive resistance and is thereby capable of reestablishing the sinus tarsi 114 to about a normal width W, yet still permits some resilience permitting normal relative motion between the talus 106 and the calcaneus 108 during normal use of the repaired foot 200.

To provide ARP 104, for at least one embodiment, skin may be harvested from a healthy donor, who has been screened for a plurality of viral, bacterial, and fungal diseases and aliments. In addition, it is expected that the donor will have a healthy past medical and social history as per AATB standards. Skin tissue of this type is generally removed by, and available from, accredited US Tissue Banks which operate under strict aseptic conditions.

If not previously processed, the dermis may be separated from the epidermis using a skin splitter, such as but not limited to the Aesculap Acculan 3Ti Dermatome which permits adjusted thickness from 0.2 to 1.2 mm in lockable 1/10 mm increments. This recovered dermis is then processed to remove the cellular components and leave the extracellular matrix and scaffold. This resulting extracellular matrix and scaffold will then be dried. For at least one embodiment, this drying is performed using traditional lyophilizing techniques, leaving approximately 10-15% moisture residue in the tissue.

As shown in FIG. 11, a reticular dermis element 1100 that has been processed as described above is shown. For at least one alternative embodiment, a plurality of dermis elements 1100 may be stacked, as shown in stack 1102.

Either as a single sheet, or stack 1102, the processed dermis 1100 is then tightly rolled into rods 1104 having desired diameters. Corresponding to the above discussion, it will be understood and appreciated that a resulting rod has a diameter about equal to the average width W of the sinus tarsi 114. Additional rods having diameters larger then the average width of the sinus tarsi 114 and smaller than the average width of the sinus tarsis 114 are also provided in accordance with at least one embodiment.

Each rod is then cut to provide the allograft rod plugs, i.e. ARP 104. For at least one embodiment the length of the each ARP 104 is about 25 mm. Each ARP 104 is then individually packaged. For at least one embodiment these individual packages are DuPont™ Tyvek® pouches made of high-density polyethylene which is extremely stable when exposed to sterility gases and high-energy sterilization processes.

Once packaged, the ARP 104 implants will undergo a second drying. Once again, for at least one embodiment this second drying process is a performed using traditional lyophilizing techniques for freeze drying, leaving approximately about 4% to 6% residual moisture within each ARP 104. This freeze drying per AAATB standards is sufficient to maintain the rod shape and preserve each ARP 104 for long term storage.

Moreover, for at least one embodiment a plurality of ARPs 104 along with corresponding spacers 706, and a Kirschner wire to act as guide may be pre-packaged as a repair non-binding allograft subtalar joint implant kit.

Of course it should be understood and appreciated that the above methods, system and structures may be adapted and applied to other similar reconstructions of other joints and/or body appendages, such as for example the human hand.

Changes may be made in the above methods, systems and structures without departing from the scope hereof. It should thus be noted that the matter contained in the above description and/or shown in the accompanying drawings should be interpreted as illustrative and not in a limiting sense. Indeed many other embodiments are feasible and possible, as will be evident to one of ordinary skill in the art. The claims that follow are not limited by or to the embodiments discussed herein, but are limited solely by their terms and the Doctrine of Equivalents.

What is claimed is:

1. A method to provide a non-binding allograft subtalar joint implant into a person's foot proximate to the ankle comprising:
   surgically accessing a canal within a person's foot proximate to the person's talus and calcaneus bones, the canal having a width between the talus and calcaneus bones;

selecting a pre-formed allograft rod plug having a diameter of about the canal width and a density sufficient to resist full compression of the canal, the pre-formed allograft rod plug being resiliently compressible and flexible while remaining substantially as the formed plug;

disposing the selected pre-formed allograft rod plug snuggly within the canal and adjacent to the talus and calcaneus bones, the pre-formed rod plug stabilizing a relative alignment between the talus and calcaneus bones while permitting relative sliding between the talus and calcaneus;

evaluating a range of motion of the foot;

in response to an abnormal range of motion, removing the pre-formed allograft rod plug and trimming at least a portion of the pre-formed allograft rod plug and redisposing the trimmed pre-formed allograft rod plug within the canal to re-evaluate the range of motion; and in response to a normal range of motion, surgically closing access to the canal.

2. The method of claim 1, wherein the pre-formed allograft rod plug is non-binding to the talus and calcaneus bones.

3. The method of claim 1, wherein the pre-formed allograft rod plug compresses during pronation of the person's foot and expands back to about the diameter of the canal and maintains the canal in an anatomically correct alignment and reduces a tendency for abnormal motion between the person's talus and calcaneus bones.

4. The method of claim 1, wherein the pre-formed allograft rod plug is generally acellular dermis.

5. The method of claim 1, wherein the pre-formed allograft rod plug is provided with a length of about 25 mm and a diameter selected from the group consisting of, about 8 mm, about 10 mm, and about 12 mm.

6. The method of claim 1, further including removing fatty tissue from the canal.

7. The method of claim 1, further including determining a maximum width in the canal between the talus and calcaneus bones prior to the selection of the pre-formed allograft rod plug.

8. The method of claim 7, wherein determining the maximum width between the talus and calcaneus bones is performed with spacers of varying diameters correlating to allograph rod plugs of varying diameters, disposed within the canal with a kirschner wire.

9. The method of claim 1, further including pre-trimming the selected pre-formed allograft rod plug prior to disposing selected pre-formed allograft rod plug within the canal.

10. The method of claim 1, wherein in response to an abnormal range of motion, alternatively removing the pre-formed allograft rod plug and selecting a second pre-formed allograft rod plug having a different diameter size and disposing the second pre-formed allograft rod plug snuggly within the sinus tarsi to re-evaluate the range of motion.

11. The method of claim 1, wherein the canal is a sinus tarsi.

12. The method of claim 1, wherein the canal is an opening of a subtalar joint of the person's foot.

13. The method of claim 1, wherein the normal range of motion is no more than 4 degrees of relative motion.

14. The method of claim 1, wherein the pre-formed allograft rod plug is provided by:

harvesting at least one reticular dermis element from at least one donor;

processing the reticular dermis element to remove cellular component and leave extracellular matrix and scaffold, and drying the reticular dermis element;

rolling the processed reticular dermis element into a rod;

cutting the rod into pre-determined lengths;

freeze drying each cut length; and packaging each freeze dried cut length.

15. The method of claim 14, wherein each reticular dermis element is between about 1-3 mm thick and has about 4 to 12 cubic centimeters of dermis.

16. The method of claim 14, wherein the freeze drying results in less than about 4 to 6% residual moisture within each cut length.

17. The method of claim 1, wherein the plug cannot be unrolled.

18. The method of claim 1, wherein the plug cannot be unfolded.

19. A method to provide a non-binding allograft subtalar implant into a person's foot proximate to the ankle comprising:

surgically accessing a sinus tarsi within a person's foot proximate to the person's talus and calcaneus bones;

extracting a fatty tissue plug from the sinus tarsi;

determining a maximum width within the canal between the talus and calcaneus bones;

selecting a pre-formed allograft rod plug having a diameter of about an equivalent size to the determined maximum width of the canal and a density sufficient to resist full compression of the canal, the pre-formed allograft rod plug being resiliently compressible and flexible while remaining substantially as the formed plug;

disposing the selected pre-formed allograft rod plug snuggly within the sinus tarsi and adjacent to the talus and calcaneus bones, the pre-formed rod plug stabilizing a relative alignment between the talus and calcaneus bones while permitting relative sliding between the talus and calcaneus bones;

evaluating a range of motion of the foot;

in response to an abnormal range of motion, removing the pre-formed allograft rod plug and in a first instance trimming at least a portion of the pre-formed allograft rod plug and redisposing the trimmed pre-formed allograft rod plug snuggly within the sinus tarsi to re-evaluate the range of motion, and in a second instance selecting a second pre-formed allograft rod plug having a different diameter size and disposing the second pre-formed allograft rod plug snuggly within the sinus tarsi to re-evaluate the range of motion; and in response to a normal range of motion, surgically closing access to the sinus tarsi.

20. The method of claim 19, wherein the pre-formed allograft rod plug is non-binding to the talus and calcaneus bones.

21. The method of claim 19, wherein the pre-formed allograft rod plug compresses during normal use of the person's foot and expands back to about the diameter of the canal and maintains the canal in an anatomically correct alignment and reduces a tendency for abnormal motion between the person's talus and calcaneus.

22. The method of claim 19, wherein the pre-formed allograft rod plug is generally acellular dermis.

23. The method of claim 19, further including pre-trimming the selected pre-formed allograft rod plug prior to disposing selected pre-formed allograft rod plug within the canal.

24. The method of claim 19, wherein the pre-formed allograft rod plug is provided with a length of about 25 mm and a diameter selected from the group consisting of about 8 mm, about 10 mm, and about 12 mm.

25. The method of claim 19, wherein determining the maximum width between the talus and calcaneus bones is performed with spacers of varying diameters correlating to allograph rod plugs of varying diameters disposed within the sinus tarsi with a kirschner wire.

26. The method of claim 19, wherein the normal range of motion is no more than 4 degrees of relative motion.

27. The method of claim 19, wherein the pre-formed allograft rod plug is provided by:
  harvesting at least one reticular dermis element from at least one donor;
  processing the reticular dermis element to remove cellular component and leave extracellular matrix and scaffold, and drying the reticular dermis element;
  rolling the processed reticular dermis element into a rod;
  cutting the rod into pre-determined lengths;
  freeze drying each cut length; and
  packaging each freeze dried cut length.

28. The method of claim 27, wherein each reticular dermis element is between about 1-3 mm thick and has about 4 to 12 cubic centimeters of dermis.

29. The method of claim 27, wherein the freeze drying results in less than 4%-6% residual moisture within each cut length.

30. The method of claim 19, wherein the plug cannot be unrolled.

31. The method of claim 19, wherein the plug cannot be unfolded.

\* \* \* \* \*